(12) United States Patent
Volpi et al.

(10) Patent No.: US 12,365,141 B2
(45) Date of Patent: Jul. 22, 2025

(54) PROCESS FOR THE PRODUCTION OF A 4D MEDICAL DEVICE AND 4D MEDICAL DEVICE

(71) Applicant: 3D MEDLAB, Marignane (FR)

(72) Inventors: Gaël Volpi, La Motte D'Aigues (FR); Donatien Campion, Marseilles (FR); Marie Fischer, Aix-en-Provence (FR)

(73) Assignee: 3D MEDLAB, Marignane (FR)

( * ) Notice: Subject to any disclaimer, the term of this patent is extended or adjusted under 35 U.S.C. 154(b) by 1177 days.

(21) Appl. No.: 16/950,559

(22) Filed: Nov. 17, 2020

(65) Prior Publication Data

US 2021/0146630 A1 May 20, 2021

(30) Foreign Application Priority Data

Nov. 18, 2019 (FR) ...................................... 1912859

(51) Int. Cl.
*G06F 30/20* (2020.01)
*A61F 2/90* (2013.01)
(Continued)

(52) U.S. Cl.
CPC .............. *B29C 64/393* (2017.08); *A61F 2/90* (2013.01); *B22F 3/24* (2013.01); *B33Y 50/02* (2014.12);
(Continued)

(58) Field of Classification Search
CPC ......... G06F 30/20; G16H 30/20; B33Y 50/02; B33Y 80/00; A61F 2/90; A61F 2240/002;
(Continued)

(56) References Cited

U.S. PATENT DOCUMENTS 9,114,032 B1 8/2015 Pulugurtha
2009/0024152 A1 1/2009 Boyden et al.
(Continued)

FOREIGN PATENT DOCUMENTS

WO WO 2018/195189 A1 10/2018

OTHER PUBLICATIONS

Preliminary Search Report for French Application Serial No. 1912859 (Oct. 6, 2020).

*Primary Examiner* — Andre Pierre Louis
(74) *Attorney, Agent, or Firm* — Jenkins, Taylor & Hunt, P.A.

(57) ABSTRACT

The subject matter described herein relates to a process suitable for the production of an implantable medical device by means of a 3D printer. The process includes identifying an intended implant area for the medical device, collecting, in a non-invasive manner, a set of physiological data corresponding to the local anatomy of said intended implant area of the patient, noninvasively taking measurements from the set of physiological data of the patient with the aid of an analysis tool, and adding the characteristics of the medical device, which are specific to additive manufacturing, to thus generate a 3D model of the medical device to be produced. The process further includes exporting the 3D model of the medical device to be produced to the 3D printer suitable for printing a shape-memory material in which the parameters of the 3D printer are adapted to the geometry of the medical device.

18 Claims, 1 Drawing Sheet

(51) Int. Cl.

| | |
|---|---|
| *B22F 3/24* | (2006.01) |
| *B29C 64/393* | (2017.01) |
| *B33Y 50/02* | (2015.01) |
| *B33Y 80/00* | (2015.01) |
| *G16H 30/20* | (2018.01) |
| *B22F 10/36* | (2021.01) |
| *B22F 10/60* | (2021.01) |
| *B22F 10/80* | (2021.01) |
| *B33Y 50/00* | (2015.01) |
| *G16H 30/40* | (2018.01) |

(52) U.S. Cl.
CPC .............. *B33Y 80/00* (2014.12); *G16H 30/20* (2018.01); *A61F 2240/002* (2013.01); *A61F 2250/0092* (2013.01); *B22F 10/36* (2021.01); *B22F 10/60* (2021.01); *B22F 10/80* (2021.01); *B33Y 50/00* (2014.12); *G16H 30/40* (2018.01)

(58) Field of Classification Search
CPC ... A61F 2250/0092; B22F 3/24; B29C 64/393
USPC ............................................................ 703/1
See application file for complete search history.

(56) References Cited

U.S. PATENT DOCUMENTS

| | | | |
|---|---|---|---|
| 2013/0144573 A1 | 6/2013 | Sharma et al. | |
| 2015/0209162 A1 | 7/2015 | Verschueren et al. | |
| 2017/0022111 A1* | 1/2017 | Jarvis | A61F 2/28 |
| 2019/0231361 A1* | 8/2019 | Cooper | A61B 17/12109 |
| 2019/0328517 A1* | 10/2019 | Prawel | B33Y 10/00 |
| 2020/0049415 A1* | 2/2020 | Schiffres | F28D 15/046 |
| 2021/0192759 A1* | 6/2021 | Lang | A61B 34/20 |

* cited by examiner

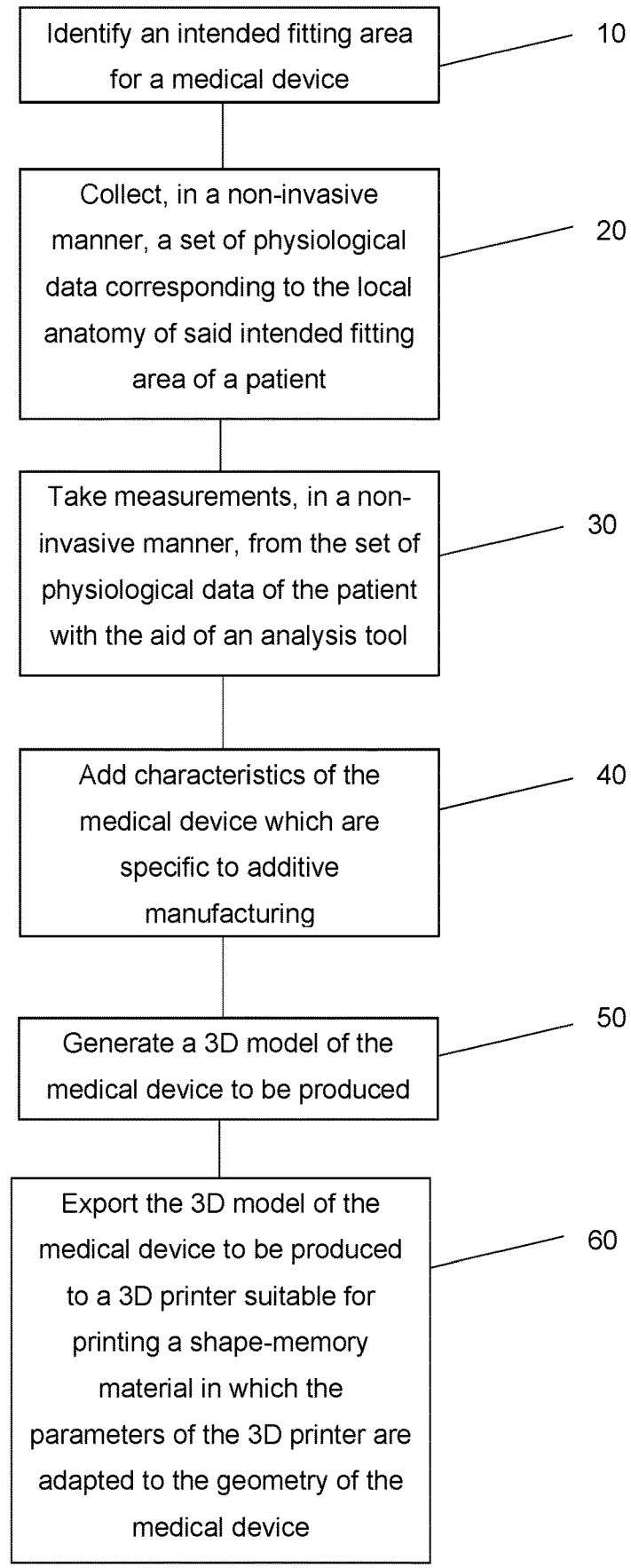

PROCESS FOR THE PRODUCTION OF A 4D MEDICAL DEVICE AND 4D MEDICAL DEVICE

FIELD OF THE INVENTION

The invention relates to a process that makes it possible to produce a medical device using additive manufacturing. The invention relates in particular to the shape, production and post-processing of a four-dimensional (4D) medical implant in the vascular field, especially the cardiovascular, neurovascular and gastrovascular fields. The invention also relates to a medical device obtained with the aid of said process.

STATE OF THE ART

Currently, it is possible to use additive manufacturing to obtain medical devices, for example, medical devices in the vascular field, such as stents. In addition, four-dimensional (4D) medical implants can be made with the aid of certain traditional manufacturing processes (machining, laser cutting of plates, of tubes, filament winding or weaving, etc.).

However, the 4D medical devices which are produced with the aid of traditional manufacturing methods are not always specific to a given patient. This means that the medical devices currently used in the vascular field are non-customised devices, which are based on stresses of average anatomy. Consequently, when this type of device is fitted, the device that is most suitable for a given patient is selected from devices which are non-customised and available. The use of this type of device does not guarantee that the fitted device offers optimal characteristics for the patient in question. In addition, this type of device does not necessarily have characteristics which are optimal for the medical purpose sought. In some cases, a device of size can be used. This device is therefore soiled then discarded, and a device of the correct size is then fitted.

It should be noted that additive manufacturing makes it possible to produce medical devices which are specific to a given patient. However, the constraints in terms of process and choice of materials imply that vascular implants are not made by additive manufacturing. Additive manufacturing is therefore predominantly used for manufacturing devices which are specific to a given patient in the field of orthopedics, by way of the making of hip prostheses and knee prostheses, for example.

The use of shape-memory materials for these devices offers the advantage by which the devices can be inserted into the human body, in a first insertion position by a path which is firstly percutaneous, relatively compact and can, once put in place, be deployed towards their second position of use. In addition, the method of deployment of the medical device can be totally governed by the natural behaviour of the 4D material. Consequently, actuators are not necessary in order to perform this deployment.

By contrast, the techniques currently used to obtain medical devices which are customised for a given patient in shape-memory materials are not suitable for cost-effective production of such medical devices.

The U.S. Pat. No. 9,114,032 discloses a process for manufacturing a stent comprising a three-dimensional printer receiving a set of data corresponding to a precursor stent in three dimensions. The printer in three dimensions produces a precursor stent. The precursor stent comprises a plurality of webs arrange adjacent to one another, each web comprising a plurality of spacers which are connected by a plurality of collars and a plurality of connectors linking each web to an adjacent web. Next, the precursor stent is processed to remove a defined number of the plurality of connectors between adjacent webs, so that at least one connector between each set of adjacent webs is removed. The use of 3D printing is therefore confined to the production of a non-finalised device. The U.S. Pat. No. 9,114,032 discloses the possibility of obtaining stents of a standard dimension, which are made with the aid of a three-dimensional printer. The U.S. Pat. No. 9,114,032 does not disclose the possibility of obtaining stents which offer customised dimensions.

In the light of the observations above, the aim of the invention is to provide a process allowing the production of a medical device using additive manufacturing in a shape-memory material. The invention relates in particular to the shape, the production of the device in its final geometry and the post-processing of a 4D medical implant that does not have an impact on the integrity of the structure created.

SUMMARY OF THE INVENTION

The present invention relates to a process suitable for the production of a medical device by means of a three-dimensional (3D) printer, said medical device being intended to be implanted in the body of a patient, comprising the following steps:
- identifying an intended implant area for the medical device,
- collecting, in a non-invasive manner, a set of physiological data corresponding to the local anatomy of said intended implant area of the patient,
- taking measurements, in a non-invasive manner, from the set of physiological data of the patient with the aid of an analysis tool,
- adding the characteristics of the medical device, which are specific to additive manufacturing, to thus generate a three-dimensional (3D) model of the medical device to be produced, the process then comprising the following step:
- exporting the 3D model of the medical device to be produced to the three-dimensional (3D) printer suitable for printing a shape-memory material in which the parameters of the three-dimensional (3D) printer are adapted to the geometry of the medical device.

According to a preferred embodiment, the step that makes it possible to take measurements from the set of physiological data of the patient comprises the step consisting of measuring the distances between two anatomical parts.

According to a preferred embodiment, the step that makes it possible to take measurements from the set of physiological data of the patient comprises the step consisting of obtaining an anatomical shape.

According to a preferred embodiment, the set of physiological data is presented in the form of patient images extracted from a DICOM (Digital Imaging and Communication in Medicine) file, from a scanner or from a scintigraphy scan.

According to a preferred embodiment, the set of physiological data comprises the mechanical properties of a tissue in said intended fitting area of the patient.

According to a preferred embodiment, the characteristics of the medical device, which are specific to additive manufacturing, comprise lattice structures.

According to a preferred embodiment, the characteristics of the medical device, which are specific to additive manufacturing, comprise a customisation of the thickness of the medical device depending on the stresses which will be applied to said medical device.

According to a preferred embodiment, a geometric landmark is added to the design of the medical device in order to be able to verify the axial positioning.

According to a preferred embodiment, the shape-memory material mainly comprises the components nickel and titanium.

According to a preferred embodiment, the shape-memory material comprises an alloy with 55.4% nickel and 44.6% titanium, by weight.

According to a preferred embodiment, the material is in the form of a powder whose particle sizing is between 1 micrometre and 100 micrometres.

According to a preferred embodiment, the 3D printer comprises an energy source that allows the melting of a material, in a local manner.

According to a preferred embodiment, the energy source is controlled in terms of speed and power, with values of between 1 mm/s and 10,000 mm/s and of between 1 W and 5000 W, respectively.

According to a preferred embodiment, said energy source comprises a laser such as a YAG, yttrium or $CO_2$ laser.

According to a preferred embodiment, the process comprises, after the step of producing the medical device, a post-processings step that makes it possible to increase or adapt the mechanical properties of said medical device or of the exterior surface of said medical device.

According to a preferred embodiment, the post-processings step comprises sanding, microbeading, shot-peening, passivation, electroplating, static chemical deposition, dynamic chemical deposition, polishing, heat treatment or chemical machining.

According to a preferred embodiment, the medical device is a stent.

The present invention also relates to a computer programme comprising computer programme code means that make it possible to perform the steps when said programme is run on a computer.

BRIEF DESCRIPTION OF THE DRAWINGS

The aim, subject and characteristics of the invention will become more clearly apparent on reading the following description with reference to the FIGURE, in which:

FIG. 1 shows the steps of the process according to the invention.

DETAILED DESCRIPTION

The invention relates in particular to the shape, production and post-processing of a medical device made of a shape-memory material with the aid of an additive manufacturing process. In the context of this text, the term "4D printing" refers to the production of device in such a shape-memory material with the aid of an additive manufacturing process. This definition is associated with modification of the geometry produced or of the behaviour of the material over time as the result of an external factor such as, but not limited to, a variation in temperature, a chemical reaction or mechanical stress.

In the description that follows, for exemplary reasons, reference is made to a stent. In the context of this text, the term stent is used to refer to any medical device that is suitable for being implanted in a passage, inside a human body for example, in a temporary or permanent manner.

The content of the description refers to a shape-memory material. In the context of said description, the term "shape-memory material" refers to a shape-memory alloy (SMA) that possesses several particular properties. A shape-memory material has the ability to remember an initial shape and to regain this shape even after deformation. In addition, a material such as this has the possibility to alternate between two previously memorised shapes when an external factor, such as its temperature for example, varies around a critical temperature, as the result of a chemical interaction with another component or in response to a mechanical stimulus. Moreover, a material such as this offers "super-elastic" behaviour that enables stretching, without permanent deformation, that is greater than that offered by other metals. A whole variety of alloys with nickel and titanium as the main constituents, in almost equal proportions, can be found amongst the main shape-memory alloys.

Although "nitinol" is in fact only the name of one of these quasi-equiatomic nickel-titanium alloys, this denomination has become commonly used in the literature to denote all of these alloys, which offer very similar properties.

The process according to the invention comprises several steps, as explained in succession hereinbelow. It is important to note that, if necessary, the order of the steps mentioned below can be reversed.

In order that the process according to the invention is able to be initiated, and before undertaking the implantation of a medical device in a living being, for example a human being, it is advisable to consult a doctor. Said doctor determines, on the one hand, the location where the medical device must be positioned in a step 10 and, on the other hand, the requirements for operation of said medical device.

The process according to the invention relating to the production of the medical device comprises a first step 20 comprising the collection, in a non-invasive manner, of a set of physiological data corresponding to the local anatomy of the patient.

Said set of physiological data can take several forms. Said data is obtained, for example, with the aid of a scanner, an MRI (Magnetic Resonance Imaging) scan, or any other acquisition means suitable for obtaining data concerning the anatomy of the patient.

This data can take the form of patient images extracted from a DICOM (Digital Imaging and Communication in Medicine) file, from a scanner, or from a scintigraphy scan. This data can also be biomechanical data, such as the mechanical properties of a tissue or potential geometric modifications associated with a pathology. This data can also be aortic reflux flowrates or stenosis stress.

According to another step 30, measurements are taken, in a non-invasive manner, from the set of physiological data of the patient with the aid of analysis tools. These measurements are carried out in the area intended for fitting or implantation of the prosthesis and its environment. They can take the form of, but are not limited to, a measurement of distances between two anatomical parts, a measurement of a diameter, the obtaining of an anatomical shape or the delimiting of a pathological area. These measurements serve as a basis for the design of the medical device that is adapted to the pathology of the patient concerned. The medical device can be, for example, a valve support, a stent, or any other medical device of this type.

According to another step 40, the characteristics of the medical device, which are specific to additive manufacturing, are added. The objective of the invention is to produce a device that is optimised both geometrically and biomechanically. Lattice structures, a customisation of the thickness of the medical device depending on the stresses which will be applied to said medical device may be cited, for example. In addition, or alternatively, overthicknesses can be applied in order to compensate the variation in thickness during post-processings which are described hereinafter. Moreover, the supports which are necessary for production by additive manufacturing are added.

According to another step 50, the 3D model of the medical device to be produced is thus generated and is exported to the production machine in a step 60. According to the invention, said production machine is a 3D printer, suitable for printing a shape-memory material.

According to an example of the invention, the shape-memory material comprises two main components such as nickel and titanium.

According to an example of the invention, a 3D printer such as this comprises an energy source that allows the melting of a material, in a local manner. This energy source can take the form of, but is not limited to, a laser such as a YAG, yttrium or $CO_2$ laser.

In addition, a geometric landmark is added to the shape of the medical device in order to be able to check the axial positioning.

In order to optimise the characteristics produced, according to another step, the parameters of the 3D printer are adapted to each typical geometry of a medical device and mainly concern the speed and power of the laser. Depending on the properties sought, the speed can vary between 1 mm/s and approximately 10,000 mm/s. The power of the laser can vary between 1 W and 5000 W. Other criteria, such as the distance between two passes of the laser, can also be adapted.

In addition, adapting the parameterisation makes it possible to modify the threshold temperature between the two crystallographic states of the shape-memory material, and thus consequently makes it possible to adapt the opening temperature of the medical device. Depending on the material used, the parameters applied to this material, and the device made, the transition temperature between the two states is between −100° C. and +100° C. This effect comes from the behaviour of the alloy of the shape-memory material when the latter is subjected to the laser. Since the two main components of the alloy, namely nickel and titanium, do not have the same melting and evaporation temperatures, the percentage composition of the alloy can vary depending on the parameters developed and applied. For example, a composition of the NiTinol, for a shape-memory alloy, can be 55.4% nickel and 44.6% titanium, by weight. The material can be in the form of a powder whose particle sizing is between 1 micrometre and 100 micrometres.

This variation of the parameters is used in order to establish the properties to the medical device produced.

After the step of producing the medical device, and according to a sixth step, the medical device follows a series of post-processings with the aim of guaranteeing its geometric conformity and of avoiding deformations. In addition, this step makes it possible to enhance or adapt the mechanical properties of the medical device or of the exterior surface of said medical device. These post-processings can take the form of, but are not limited to, sanding, microbeading, shot-peening, passivation, electroplating, static chemical deposition, dynamic chemical deposition, polishing, heat treatment or chemical machining.

The use of shape-memory materials has necessitated the development of supplementary steps compared to a traditional post-processing process for items produced by additive manufacturing.

The items made by 3D printing require specific processings which make it possible to optimise their surface state, their mechanical properties and make it possible to check for the presence of powder on the surface of the items.

In addition, as regards the items made of shape-memory materials, specific processings are performed, heat treatments in particular. The modification of the heat properties with the aid of the parameterisation for making the medical device makes it possible to modulate the thermomechanical behaviour of the medical device.

The use of the process according to the invention offers a possibility according to which the medical device thus obtained will be specific to each patient, whether it be from a geometric point of view, by following the geometry of the local anatomy, but also from a mechanical point of view, by applying exactly the necessary force to the tissues which are present in the environment where the medical device is installed.

EXAMPLE

The invention can offer applications in the vascular field and also in the cardiovascular, gastrovascular and neurovascular fields and in the field of vascularisation of the spine.

In particular, the process according to the invention can be used for the production of stents. Tailor-made stents are first of all deployed via the transcatheter route without having recourse to a complex mechanism, and consequently can reduce the risks associated with surgery. For example, by virtue of the shape and characteristics of the device obtained, it is possible to facilitate surgical intervention on a patient. Another example resides in the fact that the use of the material to be sterilised can be improved by virtue of the shape and characteristics of the medical device obtained.

In the same way, the process according to the invention can be used in the case of aortic valve support.

In the case of dimensioning that is specific to the patient, the medical device according to the invention offers increased performance compared to a standard medical device. Indeed, a non-customised device such as a TAVI (Transcatheter Aortic Valve Implantation) valve support has cylindrical sections, whereas the aorta and the annulus are not perfectly cylindrical anatomies. This brings a risk of peripheral leakage, with drug management being necessary to increase blood viscosity. This causes a risk of thrombosis and erectile complications in men, for example. Now, since the medical device according to the invention is a tailor-made prosthesis, it is possible to reduce the risk and to make drug management non-essential.

The advantage of the invention compared to the solutions which are currently available resides in the combination of the use of shape-memory materials and the freedom of design and speed of production of additive manufacturing.

In the context of vascular applications, the use of shape-memory materials makes it possible to compress medical devices in order to facilitate the positioning and handling thereof in the human body, before being deployed naturally by virtue of the properties of the shape-memory material to regain its initial shape following an increase in temperature above a specified threshold value.

The freedom of design offered by additive manufacturing makes it possible to adapt the shape of the medical device to the geometry of the human body of the patient. This customisation makes it possible to improve the performance of the medical device. This improvement in performance is a combination of mechanical performance adapted to the geometry of the human body of a patient and the shape which is also adapted to the geometry of the human body of the patient.

Implementation by additive manufacture of this type of medical device consequently makes it possible to circumvent the long processing times and geometric constraints associated with the processes of the state of the art, and thus to produce medical devices which are optimised for the patients.

In addition, the modification of the heat properties with the aid of the parameterisation for making the item makes it possible to modulate the thermomechanical behaviour of the medical device. The mechanical behaviour can be isotropic or anisotropic, in the case of an optimised melting strategy where some areas of the device have a behaviour associated with the retention of the device in its environment (main ring or grip) whereas other areas have functions to do with maintaining the vascular structure, for example optimisation of the fatigue resistance.

Complete Example of a Diagram for Making a Medical Device:

A surgeon transfers a patient imagery file to the designer in the form of a DICOM file. The patient is suffering from an aortic insufficiency, and an operation to replace the aortic valve is scheduled in order to correct this pathology.

The imagery is imported into software in order to extract therefrom the geometric data necessary for the arrangement of the medical device.

Landmarks are placed, in a non-invasive manner, in the intended fitting or implant area, that is to say on the ascending aorta. These landmarks make it possible to measure the diameters on different sections, the shape of different sections, and the length of the intended area. Other extracted information is the thicknesses of the aortic tissues and the pathological deformations. These values are individual to each patient, and depend upon the pathology of the patient. Potentially, a 3D model of the anatomy of the patient can be printed in order to test the mounting of the prosthesis before the surgical operation is performed. These values serve as input data for making the prosthesis.

The scheduled procedure is a fitting of an aortic support by the TAVI method. The information extracted from the data of the patients is used in order to dimension the medical device. The shape of the prosthesis is adapted in order to correspond perfectly to the anatomy of the patient. Depending on the different aorta thicknesses, the thickness of the device is modified at points and lattice structures are added in certain areas to add rigidity to the device. Finally, the CAD (Computer-Aided Design) file of the device is divided into different areas in order to allocate a different parameterisation thereto. The shape is also adapted in order to offer a transition area between the production platform and the device. For example, in the case where an aorta has areas where the diameter is reduced, lattice structures can be added to the device to guarantee sufficient rigidity so that the device is not deformed.

Depending on the material selected and the areas divided during the design of the device, different parameterisations are applied to the medical item or device to be produced. In the area where it is desired to obtain super-elastic behaviour, the energy supply strategy will be a high-speed, high-power strategy, with, for example, in the case of a NiTinol alloy, a power of 140 W for a speed of 1200 mm/s. In the area where it is desired to obtain shape-memory behaviour, the energy supply strategy will be a low-speed, low-power strategy, with, for example, in the case of a NiTinol alloy, a power of 25 W for a speed of 100 mm/s.

Next, the production data is sent to the machine used for producing the item. In the precise case of the stent, the machine used is a DMLS (Direct Metal Laser Sintering) machine. The machine is prepared by verifying especially the amount of powder available in the machine, the cleanliness of the production chamber and of the lenses, the planarity of the production platform and the level of the powder scraper. The item can then be produced by the selected machine When production is finished, the powder is removed from the machine and the machine is cleaned, and the platform is removed from the machine. In this precise case, no heat treatment is performed on the item.

The item is manually unhooked from the platform. A first cleaning step takes place. In this step, the item is immersed in an ultrasonic bath for 30 minutes. In this bath, the item is immersed in diluted alcohol and the bathing is carried out at ambient temperature.

In order to improve its surface state, after cleaning in the ultrasonic bath, the item is sanded with hydroxyapatite as the sanding medium.

After these steps, the item follows a conventional implant-cleaning process before it is fitted.

What is claimed is:

1. A process for producing a medical device by means of a three-dimensional (3D) printer, said medical device being intended to be implanted in the body of a patient, comprising the following steps:
   identifying an intended implant area for the medical device,
   collecting, with the aid of an acquisition means and in a non-invasive manner, a set of physiological data corresponding to local anatomy of said intended implant area of the patient,
   taking measurements, with the aid of analysis tools and in a non-invasive manner, from the set of physiological data of the patient,
   adding characteristics of the medical device, which are specific to additive manufacturing, to thus generate a 3D model of the medical device to be produced, the process then comprising the following step:
   exporting the 3D model of the medical device to be produced to the 3D printer suitable for printing a shape-memory material in which parameters of the 3D printer are adapted to a geometry of the medical device; and
   3D printing, using the 3D printer, the shape memory material, and according to the 3D model, the medical device, wherein the medical device comprises an implantable vascular device having dimensions customized to the patient based on the measurements, and the shape memory material is configured to alternate between two crystallographic states by varying a temperature of the shape memory material, and the method further comprises modifying a transition temperature of the shape memory material that causes the shape memory material to transition between the two crystallographic states and thereby change an opening temperature of the implantable vascular device.

2. The process according to claim 1, wherein taking the measurements from the set of physiological data of the patient comprises the step of:
   measuring distances between two anatomical parts.

3. The process according to claim 1, wherein taking the measurements from the set of physiological data of the patient comprises the step of:
obtaining an anatomical shape.

4. The process according to claim 1, wherein the set of physiological data is presented in the form of patient images extracted from a DICOM (Digital Imaging and Communication in Medicine) file, from a scanner or from a scintigraphy scan.

5. The process according to claim 1, wherein the set of physiological data comprises mechanical properties of a tissue in said intended implant area of the patient.

6. The process according to claim 1, wherein the characteristics of the medical device, which are specific to additive manufacturing, comprise lattice structures.

7. The process according to claim 1, wherein the characteristics of the medical device, which are specific to additive manufacturing, comprise a customization of thickness of the medical device depending on stresses which will be applied to said medical device.

8. The process according to claim 1, wherein a geometric landmark is added to a shape of the medical device in order to be able to verify axial positioning.

9. The process according to claim 1, wherein the shape-memory material mainly comprises nickel and titanium.

10. The process according to claim 9, wherein the shape-memory material comprises an alloy with 55.4% nickel and 44.6% titanium, by weight.

11. The process according to claim 1, wherein the shape-memory material is in the form of a powder whose particle sizing is between 1 micrometer and 100 micrometers.

12. The process according to claim 1, wherein the 3D printer comprises an energy source that allows melting of a material, in a local manner.

13. The process according to claim 12, wherein the energy source is controlled in terms of speed and power, with values of between 1 mm/s and 10,000 mm/s and of between 1 W and 5000 W, respectively.

14. The process according to claim 12, wherein said energy source comprises a laser, including a YAG, yttrium or $CO_2$ laser.

15. The process according to claim 1, comprising, after 3D printing the medical device, applying a post-processing step to the medical device to enhance geometric conformity or avoid deformations of the medical device.

16. The process according to claim 15, wherein the post-processing step comprises sanding, microbeading, shot-peening, passivation, electroplating, static chemical deposition, dynamic chemical deposition, polishing, heat treatment or chemical machining.

17. The process according to claim 1, wherein the medical device is a stent.

18. A computer program comprising computer program code means that make it possible to perform the steps according to claim 1 when said program is run on a computer.

* * * * *